United States Patent
Yamashita et al.

(10) Patent No.: US 9,074,188 B2
(45) Date of Patent: Jul. 7, 2015

(54) CARDIOMYOCYTE- AND/OR CARDIAC PROGENITOR CELL-PROLIFERATING AGENT AND METHOD FOR PROLIFERATING CARDIOMYOCYTES AND/OR CARDIAC PROGENITOR CELLS

(75) Inventors: Jun Yamashita, Kyoto (JP); Hideki Uosaki, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 13/885,515

(22) PCT Filed: Nov. 17, 2011

(86) PCT No.: PCT/JP2011/077266
§ 371 (c)(1),
(2), (4) Date: May 15, 2013

(87) PCT Pub. No.: WO2012/067266
PCT Pub. Date: May 24, 2012

(65) Prior Publication Data
US 2013/0244262 A1   Sep. 19, 2013

Related U.S. Application Data

(60) Provisional application No. 61/414,812, filed on Nov. 17, 2010.

(51) Int. Cl.
C12N 5/077   (2010.01)
C12N 5/0775  (2010.01)
G01N 33/50   (2006.01)

(52) U.S. Cl.
CPC ........ *C12N 5/0657* (2013.01); *C12N 2501/415* (2013.01); *C12N 5/0662* (2013.01); *C12N 2501/70* (2013.01); *C12N 2501/999* (2013.01); *C12N 2503/02* (2013.01); *G01N 33/5061* (2013.01)

(58) Field of Classification Search
CPC ........... C12N 5/0657; C12N 2501/199; C12N 2501/415
USPC .............................................. 435/325; 514/1
See application file for complete search history.

(56) References Cited

U.S. PATENT DOCUMENTS

2006/0281791 A1  12/2006  Keating et al.
2007/0009496 A1   1/2007  Adachi et al.
2007/0010012 A1   1/2007  Gold et al.
2009/0068742 A1   3/2009  Yamanaka
2011/0104122 A1   5/2011  Yamashita et al.

OTHER PUBLICATIONS

Meijer et al. 2004; Pharmacological inhibitors of glycogen synthase kinase 3. Trends in Pharmacologoical Sciences. 25(9): 471-480.*
Boguslawski et al. 2004; SU1498, an inhibitor of vascular endothelial growth factor receptor 2, causes accumulation of phophoylated ERK kinases and inhibits their activity in vivo and in vitro. J. Bio. Chem. 279(7): 5716-5724.*
Hall-Jackson et al. 1999; Paradoxical activation of Raf by a novel Raf inhibitor. Chemistry & Biology. 6: 559-568.*
Ledoux et al. 1999; Inhibitors of calmodulin-dependent protein kinases are nonspecific blockers of voltage-dependent K+ channels in vascular mytocytes. J. Pharmacology and Experimental Therapeutics. 290(3): 1165-1174.*
Schulz et al. 2002; p38 MAP kinase is a mediator of ischemic preconditionaing in pigs. Cardiovascular Research 55: 690-700.*
Yang et al. published on-line Jan. 20, 2010. Antipermeabiltity function of PEDF involves blockade of the MAP kinase/GSK/b-catenin signaling pathway and uPAR expression. Retinal Cell Biology. 51(6): 3273-3280.*
Engel et al. 2005; p38 MAP kinase inhibition enables proliferation of adult mammalian cardiomyocytes. Genes & Development. 19: 1175-1187.*
Chlopcikova et al. 2001; Neonatal rat cardiomyocytes—a model for the study of morphological, biochemical, and electrophysiological characteristics of the heart.*
Extended European Search Report for European Patent Application No. 11842105.6, dated May 14, 2014.
Backs et al., "CaM kinase II selectively signals to histone deacetylase 4 during cardiomyocyte hypertrophy," The Journal of Clinical Investigation, vol. 116(7), pp. 1853-1864 (Jul. 2006).
House et al., "Calcium/calmodulin-dependent protein kinase 11-δ isoform regulation of vascular smooth muscle cell proliferation," Am J Physiol Cell Physiol, vol. 292(6), pp. C2276-C2287 (2007).
Kahl et al., "Regulation of Cell Cycle Progression by Calcium/Calmodulin-Dependent Pathways," Endocrine Reviews, vol. 24(6), pp. 719-736 (2003).
McDevitt et al., "Proliferation of cardiomyocytes derived from human embryonic stem cells is mediated via the IGF/PI 3-kinase/Akt signaling pathway," *Journal of Molecular and Cellular Cardiology*, vol. 39(6), pp. 865-873 (2005).
Uosaki et al., "Small Molecules Inducing Robust Proliferation of Embryonic Stem Cell or Induced Pluripotent Stem Cell-derived Cardiomyocytes," Circulation, vol. 122(21), Suppl. S, p. A14894 (2010) (Abstract).
Uosaki et al., "Identification of Chemicals Inducing Cardiomyocyte Proliferation in Developmental Stage-Specific Manner with Pluripotent Stem Cells," NIH Public Access, Author Manuscript, published in final edited form as *Circ Cardiovasc Genet.*, vol. 6(6), pp. 624-633 (2013).
Zhang et al., "Cardiomyocyte Calcium and Calcium/Calmodulin-dependent Protein Kinase II: Friends or Foes?," *Recent Progress in Hormone Research*, vol. 59(1), pp. 141-168 (2004).

(Continued)

*Primary Examiner* — Karen Cochrane Carlson
(74) *Attorney, Agent, or Firm* — Knobbe, Martens, Olson & Bear, LLP

(57) ABSTRACT

A method for proliferating cardiomyocytes and/or cardiac progenitor cells is disclosed. The proliferation method includes contact with at least one compound such as a GSK3β inhibitor, ERK dephosphorylation inhibitor, Raf activator, CaMK2 inhibitor and p38 inhibitor. The cardiomyocyte and the cardiac progenitor cell may be a human cardiomyocyte or human cardiac progenitor cell and may be obtained from differentiation of induced pluripotent stem cells.

7 Claims, 5 Drawing Sheets

(56) References Cited

OTHER PUBLICATIONS

Engel, F.B. et al., FGF1/p38 MAP kinase inhibitor therapy induces cardiomyocyte mitosis, reduces scarring, and rescues function after myocardial infarction, PNAS USA, vol. 103, No. 42, pp. 15546-15551, 2006.

Fukushima, H. et al., Search for Myocardial Differentiation Promoting Low Molecular Compounds Using ES Cells, Regenerative Medicine, vol. 10 (Suppl.), p. 158, O-14-2, 2011.

Tseng, A.S. et al., The GSK-3 Inhibitor BIO Promotes Proliferation in Mammalian Cardiomyocytes, Chem. Biol., vol. 13, No. 9, pp. 957-963, 2006.

Uosaki, H. et al., Regulation of Differentiation and Proliferation of ES Cell-Derived Cardiomyocyte Using Low Molecular Compounds, Regenerative Medicine, vol. 9 (Suppl.), p. 158, O-03-5, 2010.

Uosaki, H. et al., Regulation of Differntiation and Proliferation of ES/iPS Cell-Derived Cardiomyocytes by Means of Low Molecular Compounds—Chemical Biology for Regenerative Medicine-, Regenerative Medicine, vol. 10 (Suppl.), p. 97, S-01-3, 2011.

Yan P. et al., Cyclosporin—A potently induces highly cardiogenic progenitors from embryonic stem cells, Biochem. Biophys. Res. Commun., vol. 379, pp. 115-120, 2009.

International Search Report re Application No. PCT/JP2011/077266 mailed Jan. 24, 2012.

* cited by examiner

Fig. 5
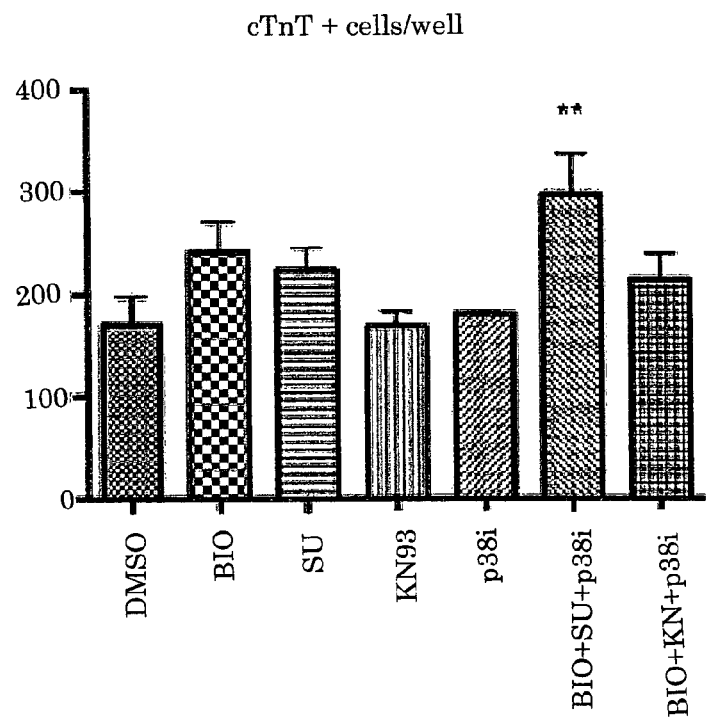
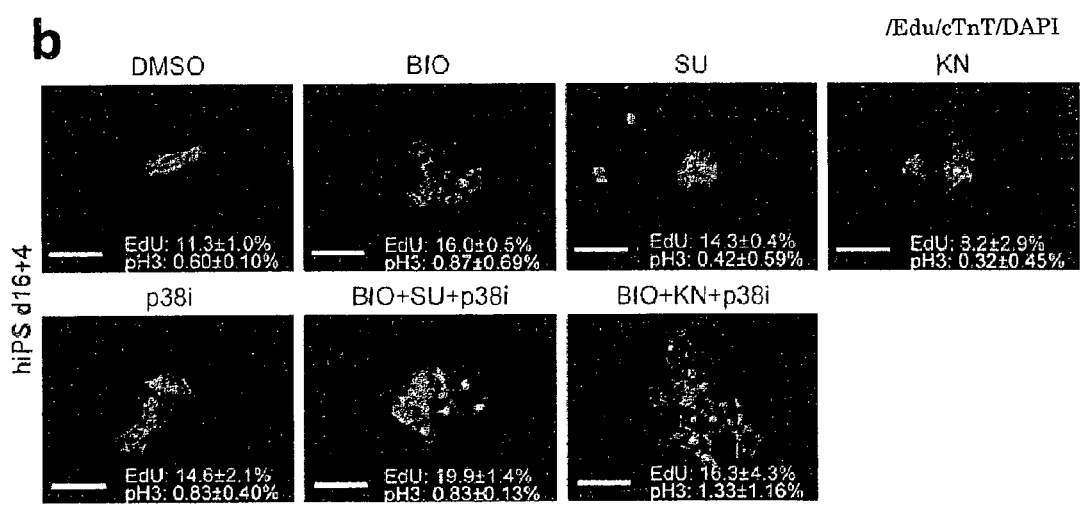

CARDIOMYOCYTE- AND/OR CARDIAC PROGENITOR CELL-PROLIFERATING AGENT AND METHOD FOR PROLIFERATING CARDIOMYOCYTES AND/OR CARDIAC PROGENITOR CELLS

CROSS-REFERENCE TO RELATED APPLICATIONS

This application is the U.S. National Phase under 35 U.S.C. §371 of International Application PCT/JP2011/077266, filed Nov. 17, 2011, which claims priority to U.S. Provisional Application No. 61/414,812, filed Nov. 17, 2010.

REFERENCE TO SEQUENCE LISTING

This application incorporates by reference the sequence listing submitted as ASCII text filed via EFS-Web on Apr. 27, 2015. The Sequence Listing is provided as a file entitled "seq 1st US TOYA166_006APC_v3.txt," created on Apr. 24, 2015, and which is approximately 3 kilobytes in size.

TECHNICAL FIELD

The present invention relates to an agent for efficient proliferation of cardiomyocytes and/or cardiac progenitor cells, and a method for efficient proliferation of cardiomyocytes and/or cardiac progenitor cells using the agent.

BACKGROUND ART

Since cardiomyocytes lose their division potential at the time of birth and hence their regeneration is difficult, recent interest has focused on replacement therapy wherein cardiomyocytes obtained by differentiation induction of cells having pluripotency (WO 2007/069666), such as embryonic stem cells (ES cells) and induced pluripotent stem cells (iPS cells), are transplanted to a cardiac tissue damaged due to myocardial infarction, myocarditis, aging or the like. Although many methods for differentiation induction of such pluripotent stem cells into cardiomyocytes have been reported (WO2007/002136, WO2009/118928 and Yan P, et al, Biochem Biophys Res Commun. 379:115-20 (2009)), there are only a small number of reports which mention proliferation of the induced cardiomyocytes. For example, as methods aiming to regenerate cardiomyocytes themselves, a method wherein nuclear-localized cyclin D1 and CDK4 are expressed to promote proliferation of cardiomyocytes (WO2005/049822) and a method using a p38 inhibitor (Engel F B, et al, Proc Natl Acad Sci USA. 103:15546-51 (2006)) have been reported.

DISCLOSURE OF THE INVENTION

The present invention aims to provide a method for efficiently proliferating cardiomyocytes and/or cardiac progenitor cells.

The inventors of the present invention screened for agents which promote proliferation of cardiomyocytes and/or cardiac progenitor cells whose differentiation was induced from mouse ES cells, and discovered that proliferation of the cells are promoted by a GSK3β inhibitor, ERK dephosphorylation inhibitor and CaMK2 inhibitor.

Subsequently, the inventors of the present invention investigated other agents having the same effects as those of the above agents and found that a Raf activator and a p38 inhibitor also function in a similar manner.

Further, the inventors of the present invention studied whether these agents show similar effects also in cardiac progenitor cells or cardiomyocytes whose differentiation was induced from human iPS cells, and confirmed that these agents promote proliferation of these cells similarly to the cells derived from mouse ES cells.

The present invention was completed based on such discoveries.

It is one aspect of the present invention to provide a cardiomyocyte- and/or cardiac progenitor cell-proliferating agent comprising at least one compound selected from the group consisting of: a GSK3β inhibitor, ERK dephosphorylation inhibitor, Raf activator, CaMK2 inhibitor and p38 inhibitor.

It is another aspect of the present invention to provide the cardiomyocyte- and/or cardiac progenitor cell-proliferating agent as described above, wherein said cardiomyocyte is a human cardiomyocyte and said cardiac progenitor cell is a human cardiac progenitor cell.

It is another aspect of the present invention to provide the cardiomyocyte- and/or cardiac progenitor cell-proliferating agent as described above, wherein said cardiomyocyte is a cardiomyocyte and/or a cardiac progenitor cell obtained by differentiation induction of pluripotent stem cells.

It is another aspect of the present invention to provide the cardiomyocyte- and/or cardiac progenitor cell-proliferating agent as described above, wherein said agent is composed of: i) a GSK3β inhibitor, CaMK2 inhibitor and p38 inhibitor; or ii) GSK3β inhibitor, ERK activator and p38 inhibitor.

It is another aspect of the present invention to provide the cardiomyocyte- and/or cardiac progenitor cell-proliferating agent as described above, wherein said agent enhances expression of CyclinA2, CyclinD2, CyclinD3, Cdk2 and cdk4 and decreases expression of Ink4b.

It is another aspect of the present invention to provide the cardiomyocyte- and/or cardiac progenitor cell-proliferating agent as described above, wherein said GSK3β inhibitor is CHIR99021 or BIO; said ERK dephosphorylation inhibitor is SU1498; said Raf activator is ZM336372; said CaMK2 inhibitor is KN62 or KN93; and said p38 inhibitor is SB203580.

It is another aspect of the present invention to provide the cardiomyocyte- and/or cardiac progenitor cell-proliferating agent as described above, wherein said agent is composed of i) BIO, SU1498 and SB203580; or ii) BIO, KN93 and SB203580.

It is another aspect of the present invention to provide a method for proliferating cardiomyocytes and/or cardiac progenitor cells, comprising culturing cardiomyocytes and/or cardiac progenitor cells in a medium comprising at least one compound selected from the group consisting of: GSK3β inhibitor, ERK dephosphorylation inhibitor, Raf activator, CaMK2 inhibitor and p38 inhibitor.

It is another aspect of the present invention to provide the method as described above, wherein said cardiomyocyte is a human cardiomyocyte and said cardiac progenitor cell is a human cardiac progenitor cell.

It is another aspect of the present invention to provide the method as described above, wherein said cardiomyocytes and/or cardiac progenitor cells are cardiomyocytes and/or cardiac progenitor cells obtained by differentiation induction of pluripotent stem cells.

It is another aspect of the present invention to provide the method as described above, wherein said agent is composed of: i) GSK3β inhibitor, CaMK2 inhibitor and p38 inhibitor; or ii) GSK3β inhibitor, ERK activator and p38 inhibitor.

It is another aspect of the present invention to provide the method as described above, wherein said agent enhances expression of CyclinA2, CyclinD2, CyclinD3, Cdk2 and cdk4 and decreases expression of Ink4b.

It is another aspect of the present invention to provide the method as described above, wherein said GSK3β inhibitor is CHIR99021 or BIO; said Raf activator is ZM336372; said ERK activator is SU1498; said CaMK2 inhibitor is KN62 or KN93; and said p38 inhibitor is SB203580.

It is another aspect of the present invention to provide the method as described above, wherein said agent is composed of: i) BIO, SU1498 and SB203580; or ii) BIO, KN93 and SB203580.

It is another aspect of the present invention to provide a method for screening a cardiomyocyte- and/or cardiac progenitor cell-proliferating agent, comprising the steps of:

(1) contacting a test substance with cardiomyocytes and/or cardiac progenitor cells obtained by differentiation induction of pluripotent stem cells;

(2) counting the number of cardiomyocytes and/or cardiac progenitor cells after step (1); and (3) selecting the test substance as a cardiomyocyte- and/or cardiac progenitor cell-proliferating agent when the number of cardiomyocytes and/or cardiac progenitor cells is larger than the number of cardiomyocytes and/or cardiac progenitor cells which are not contacted with the test substance.

It is another aspect of the present invention to provide a method for screening a cardiomyocyte- and/or cardiac progenitor cell-proliferating agent, comprising the steps of:

(1) contacting a test substance with cardiomyocytes and/or cardiac progenitor cells obtained by differentiation induction of pluripotent stem cells;

(2) counting the number of cardiomyocytes and/or cardiac progenitor cells after step (1); and (3) selecting the test substance as a cardiomyocyte- and/or cardiac progenitor cell-proliferating agent when the number of cardiomyocytes and/or cardiac progenitor cells is equivalent to or larger than the number of cardiomyocytes and/or cardiac progenitor cells which are contacted with a positive control agent having cardiomyocyte- and/or cardiac progenitor cell-proliferating ability.

It is another aspect of the present invention to provide the method as described above, wherein said positive control agent is at least one compound selected from the group consisting of GSK3β inhibitor, ERK dephosphorylation inhibitor, Raf activator, CaMK2 inhibitor and p38 inhibitor.

BRIEF DESCRIPTION OF THE DRAWINGS

FIG. 5 is a graph showing the number of troponin T type 2 (cTnT)-positive cells per well obtained when cardiomyocytes, which were derived from the human iPS cell line 253G1, were cultured with addition of each of BIO, SU (SU1498), KN93, p38i (SB203580), BIO+SU+p38i and BIO+KN+p38i (a). Immunostaining images (photograph) observed in these cases are shown in (b), wherein phosphorylation of histone 3 (pH3) is shown in gray; ethynyl uridine (EdU) is shown in yellow green; troponin T type 2 (cTnT) is shown in red; and DAPI is shown in blue. DMSO is a control wherein only a solvent was added.

DESCRIPTION OF THE PREFERRED EMBODIMENTS

Figure 1:
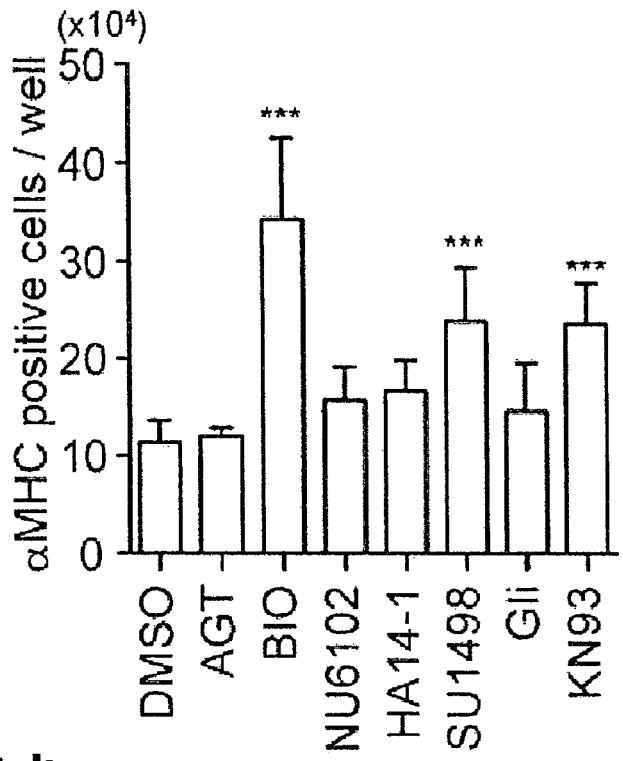
FIG. 1a is a graph showing the number of alpha-MHC-GFP-positive cells per well obtained when Flkd6, whose differentiation was induced from mouse modified ES cells EMG-7, was cultured after addition of seven agents. DMSO is a control wherein only a solvent was added.
FIG. 1b is a graph showing the number of alpha-MHC-GFP-positive cells per well obtained when Flkd6, whose differentiation was induced from EMG-7, was cultured for 2 days (Flkd6+2) or 5 days (Flkd6+5) with addition of each of BIO, SU (SU1498) and KN93. DMSO is a control wherein only a solvent was added.
Figure 1:
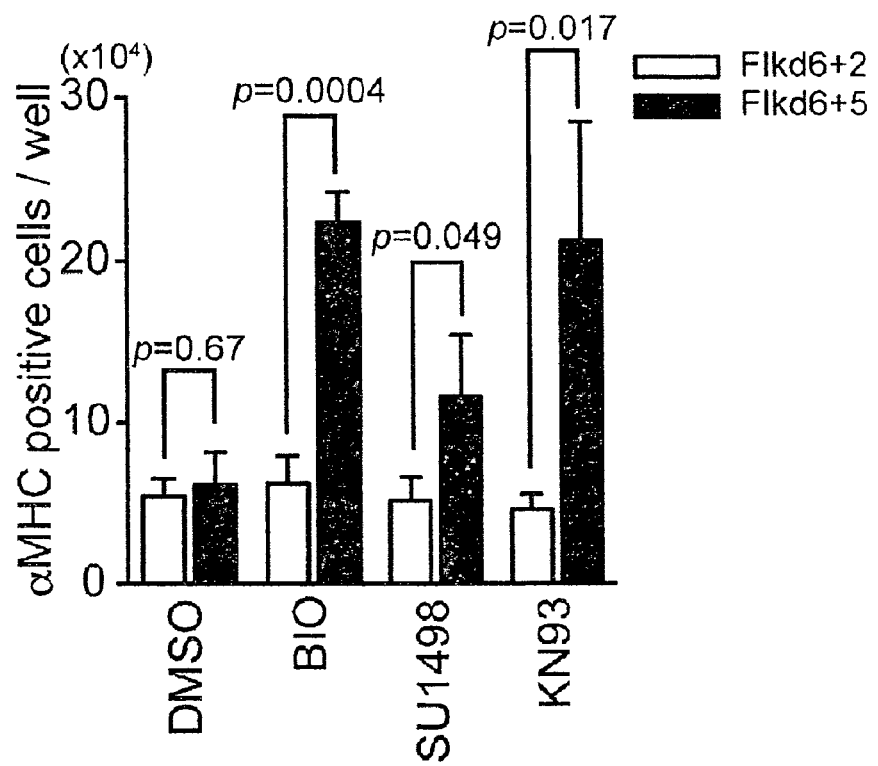
Figure 2:
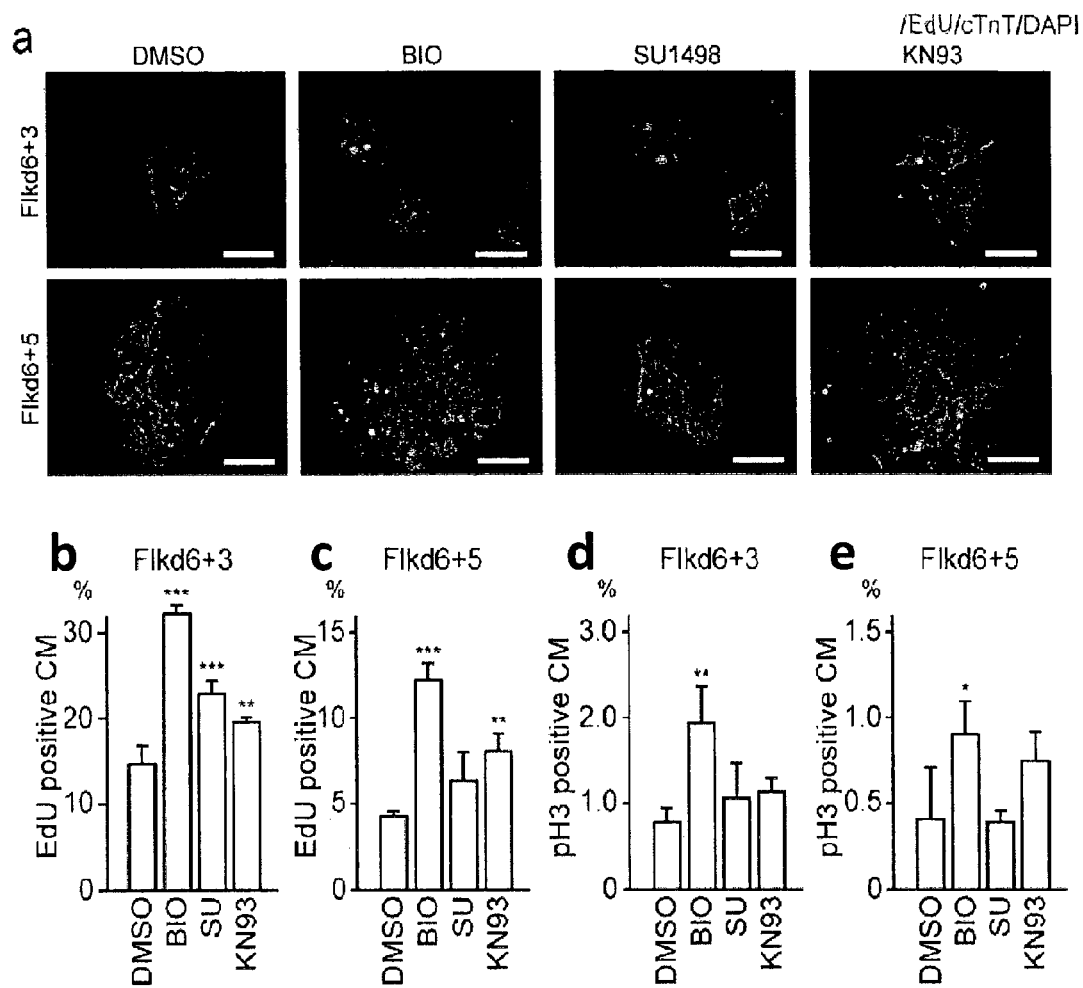
FIG. 2 shows immunostaining images (photograph) observed when Flkd6, whose differentiation was induced from EMG-7, was cultured for 3 days (Flkd6+3) and 5 days (Flkd6+5) with addition of each of BIO, SU (SU1498) and KN93, wherein phosphorylation of histone 3 (pH3) is shown in gray; ethynyl uridine (EdU) is shown in yellow green; troponin T type 2 (cTnT) is shown in red; and DAPI is shown in blue (a); and the number of positive cardiomyocyte (CM) for each staining are shown in (b) to (e). DMSO is a control wherein only a solvent was added.

The present invention provides a method for proliferating cardiomyocytes and/or cardiac progenitor cells using a GSK3β inhibitor, ERK dephosphorylation inhibitor, Raf activator, CaMK2 inhibitor and/or p38 inhibitor.

<GSK-3β Inhibitor>

The "GSK-3β inhibitor" in the present invention is defined as a compound which inhibits the kinase activity (e.g., activity to phosphorylate β catenin) of the GSK (glycogen synthase kinase)-3β protein, and many kinds of such substances are known. Particular examples thereof include BIO (also known as GSK-3β inhibitor IX; 6-bromoindirubin 3'-oxime), which is an indirubin derivative; SB216763 (3-(2,4-dichlorophenyl)-4-(1-methyl-1H-indol-3-yl)-1H-pyrrol-2,5-dione), which is a maleimide derivative; GSK-3β inhibitor VII (4-dibromoacetophenone), which is a phenyl-α-bromomethylketone compound; CHIR99021; 6-[(2-{[4-(2,4-dichlorophenyl)-5-(4-methylimidazol-2-yl)pyrimidin-2-yl]

amino}ethyl)amino]pyridine-3-carbonitrile (WO1999/65897); and L803-mts (also known as GSK-3β peptide inhibitor; Myr-N-GKEAPPAPPQSpP-NH$_2$; SEQ ID NO: 14), which is a cell membrane-permeable phosphorylated peptide; and derivatives thereof. These compounds are commercially available from Calbiochem, Biomol, Stemgen and the like, and can be easily used, but the GSK-3β inhibitor is not restricted thereto.

The subject cells may be brought into contact with the GSK-3β inhibitor by dissolving the inhibitor in an aqueous or nonaqueous solvent to an appropriate concentration and adding the resulting inhibitor solution to a suitable culture medium supplemented with about 5 to 20% fetal bovine serum (e.g., minimum essential medium (MEM), Dulbecco's modified Eagle's medium (DMEM), alpha MEM, RPMI1640 medium, 199 medium or F12 medium) such that the inhibitor concentration becomes within the range where the function of GSK-3β is sufficiently inhibited and cytotoxicity is not observed, followed by culturing the cells in the culture medium for a certain period. The inhibitor concentration varies depending on the type of the inhibitor employed, and is appropriately selected within the range of, for example, about 100 nM to about 10 μM. The contacting period is not restricted as long as it is sufficient for proliferation of the subject cells, and appropriately selected within the range of, for example, 2 days to 5 days.

<ERK Dephosphorylation Inhibitor>

The "ERK dephosphorylation inhibitor" in the present invention is defined as a compound which inhibits binding of ERK to phosphatase to thereby inhibit dephosphorylation of ERK, and examples thereof include SU1498 ((E)-3-(3,5-diisopropyl-4-hydroxyphenyl)-2-[(3-phenyl-n-propyl)aminocarbonyl]acrylonitrile) and AG1296 (6,7-dimethoxy-3-phenylquinoxaline). ERK in the present invention is exemplified by ERK1/2. Examples of the site of phosphorylation of ERK where the phosphorylation is maintained by this agent include, but are not limited to, the tyrosines at positions 202 and 204, which are described in J Biol Chem. 279, 5716 (2004). These compounds are commercially available from Calbiochem and can be easily used, but the ERK dephosphorylation inhibitor is not restricted thereto.

The subject cells may be brought into contact with the ERK dephosphorylation inhibitor by dissolving the inhibitor in an aqueous or nonaqueous solvent to an appropriate concentration and adding the resulting inhibitor solution to a suitable culture medium supplemented with about 5 to 20% fetal bovine serum (e.g., minimum essential medium (MEM), Dulbecco's modified Eagle's medium (DMEM), alpha MEM, RPMI1640 medium, 199 medium or F12 medium) such that the inhibitor concentration becomes within the range where dephosphorylation of ERK is sufficiently inhibited and cytotoxicity is not observed, followed by culturing the cells in the culture medium for a certain period. The inhibitor concentration varies depending on the type of the inhibitor employed, and is appropriately selected within the range of, for example, about 10 nM to about 10 μM. The contacting period is not restricted as long as it is sufficient for proliferation of the subject cells, and appropriately selected within the range of, for example, 2 days to 5 days.

<Raf Activator>

The "Raf activator" in the present invention is defined as a compound which activates Raf in the cells, and examples thereof include ZM336372 (3-(dimethylamino)-N-[3-[(4-hydroxybenzoyl)amino]-4-methylphenyl]benzamide). Raf in the present invention is exemplified by Raf-1. ZM336372 is commercially available from Calbiochem and can be easily used, but the Raf activator is not restricted thereto.

The subject cells may be brought into contact with the Raf activator by dissolving the activator in an aqueous or nonaqueous solvent to an appropriate concentration and adding the resulting activator solution to a suitable culture medium supplemented with about 5 to 20% fetal bovine serum (e.g., minimum essential medium (MEM), Dulbecco's modified Eagle's medium (DMEM), alpha MEM, RPMI1640 medium, 199 medium or F12 medium) such that the activator concentration becomes within the range where activation of Raf is sufficiently achieved and cytotoxicity is not observed, followed by culturing the cells in the culture medium for a certain period. The activator concentration varies depending on the type of the activator employed, and is appropriately selected within the range of, for example, about 10 nM to about 10 μM. The contacting period is not restricted as long as it is sufficient for proliferation of the subject cells, and appropriately selected within the range of, for example, 2 days to 5 days.

<CaMK2 Inhibitor>

The "CaMK2 inhibitor" in the present invention is defined as a compound which inhibits the function of CaMK2 or a compound which inhibits expression of the CaMK2 gene, and examples thereof include: (1) chemical inhibitors such as KN62 (1-[N,O-bis(5-isoquinolinesulfonyl)-N-methyl-L-tyrosyl]-4-phenylpiperazine) and KN93 (2-[N-(2-hydroxyethyl)]-N-(4-methoxybenzenesulfonyl)]amino-N-(4-chlorocinnamyl)-N-methylbenzylamine); (2) dominant negative mutants which competitively act on calmodulin-binding sites (e.g., CaMK(281-302Ala286) (amino acid sequence: MHRQEAVDCLKKFNARRKLKGA: SEQ ID NO:13) and nucleic acids encoding these; and (3) siRNAs and shRNAs against CaMK2. In the present invention, Camk2d and Camk2g are preferred isoforms of CaMK2.

The chemical inhibitors described as examples are commercially available from Calbiochem and Wako, and can be easily used, but the chemical inhibitors are not restricted to these.

The siRNAs and shRNAs against CaMK2 can be easily designed based on the sequence of CaMK2 using, for example, siRNA Target Finder provided by Ambion. Preferred examples of siRNA sequences against CaMK2 include the target sequences shown in SEQ ID NOs: 5 to 12. A single type of siRNA may be used; or plural types of siRNAs may be used at the same time. The nucleotide molecule constituting the siRNA or the shRNA may either be a wild-type RNA or have various chemical modifications in order to enhance the stability (chemically and/or enzyme resistance) and the specific activity (affinity to mRNA). For example, in order to prevent degradation by hydrolases such as nuclease, the phosphate residue (phosphate) of each nucleotide constituting the antisense nucleic acid may be substituted with a chemically modified phosphate residue such as phosphorothioate (PS), methylphosphonate or phosphorodithionate. Further, the hydroxyl group at 2'-position of the sugar (ribose) of each nucleotide may be substituted with —OR (wherein R represents CH$_3$(2'-O-Me), CH$_2$CH$_2$OCH$_3$(2'-O-MOE), CH$_2$CH$_2$NHC(NH)NH$_2$, CH$_2$CONHCH$_3$, CH$_2$CH$_2$CN or the like). Further, the base moiety (pyrimidine or purine) may be chemically modified, and examples of the chemical modification include introduction of a methyl group or a cationic functional group to 5-position of a pyrimidine base and substitution of the carbonyl group at 2-position to thiocarbonyl.

The subject cells may be brought into contact with the chemical inhibitor of CaMK2 by dissolving the inhibitor in an aqueous or nonaqueous solvent to an appropriate concentration and adding the resulting inhibitor solution to a suitable culture medium supplemented with about 5 to 20% fetal bovine serum (e.g., minimum essential medium (MEM), Dulbecco's modified Eagle's medium (DMEM), alpha MEM, RPMI1640 medium, 199 medium or F12 medium) such that the inhibitor concentration becomes within the range where CaMK2 is sufficiently inhibited and cytotoxicity is not observed, followed by culturing the cells in the culture medium for a certain period. The inhibitor concentration varies depending on the type of the inhibitor employed, and is appropriately selected within the range of, for example, about 10 nM to about 10 µM. The contacting period is not restricted as long as it is sufficient for proliferation of the subject cells, and appropriately selected within the range of, for example, 2 days to 5 days.

The subject cells may be brought into contact with the dominant negative mutant of CaMK2 by using a protein transduction method well known to those skilled in the art. Examples of such a method include methods using a protein transduction reagent, methods using a protein transduction domain (PTD)-fusion protein, and microinjection. Examples of commercially available protein transduction reagents include: BioPOTER Protein Delivery Reagent (Gene Therapy Systems), Pro-Ject™ Protein Transfection Reagent (PIERCE) and ProVectin (IMGENEX), which are cationic lipid-based; Profect-1 (Targeting Systems), which is lipid-based; and Penetrain Peptide (Q biogene) and Chariot Kit (Active Motif), which are membrane-permeable-peptide-based. The transduction can be carried out according to the manufacturer's instructions attached to these reagents.

The subject cells may be brought into contact with the siRNA or shRNA against CaMK2 directly, or in a manner wherein a vector which expresses the siRNA or shRNA against CaMK2 is brought into contact with the cells. The vector which expresses the siRNA or shRNA is prepared by, for example, linking a pol III promoter to the siRNA or shRNA to prepare an expression cassette and incorporating the resulting expression cassette to a plasmid vector or virus vector. Introduction of the plasmid vector which expresses the siRNA or shRNA, or the both, can be carried out using an introduction method well known to those skilled in the art. Examples of the method include the liposome method, polyamine method, electroporation and bead method. Examples of commercially available liposome reagents include Lipofectamine 2000, Oligofectamine (Invitrogen) and GeneEraser™ siRNA transfection reagent (Stratagene). The introduction can be carried out according to the manufacturer's instructions attached to these reagents. Further, examples of the virus vector include retroviruses, lentiviruses, adenoviruses, adeno-associated viruses and herpes viruses, which can be introduced to the cells by methods well known to those skilled in the art.

<p38 Inhibitor>

The "p38 inhibitor" in the present invention is defined as a compound which inhibits the function of the p38 protein, and examples thereof include, but are not limited to, chemical inhibitors of p38, and dominant negative mutants of p38 and nucleic acids encoding them.

Examples of the chemical inhibitors of p38 in the present invention include, but are not limited to, SB203580 (4-(4-fluorophenyl)-2-(4-methylsulfonylphenyl)-5-(4-pyridyl)-1H-imidazole) and derivatives thereof; SB202190 (4-(4-fluorophenyl)-2-(4-hydroxyphenyl)-5-(4-pyridyl)-1H-imidazole) and derivatives thereof; SB239063 (trans-4-[4-(4-fluorophenyl)-5-(2-methoxy-4-pyrimidinyl)-1H-imidazol-1-yl]cyclohexanol) and derivatives thereof; SB220025 and derivatives thereof; PD169316; RPR200765A; AMG-548; BIRB-796; SClO-469; SCIO-323; VX-702 and FR167653.

These compounds are commercially available, and, for example, SB203580, SB202190, SC239063, SB220025 and PD169316 are available from Calbiochem; and SClO-469 and SCID-323 are available from Scios and the like.

Further, examples of the dominant negative mutants of p38 include p38T180A, wherein the threonine at position 180 located in the DNA-binding region of p38 was mutated to alanine by point mutation; and p38Y182F, wherein the tyrosine at position 182 of p38 in human and mouse was mutated to phenylalanine by point mutation.

The subject cells may be brought into contact with the chemical inhibitor of p38 by dissolving the inhibitor in an aqueous or nonaqueous solvent to an appropriate concentration and adding the resulting inhibitor solution to a suitable culture medium supplemented with about 5 to 20% fetal bovine serum (e.g., minimum essential medium (MEM), Dulbecco's modified Eagle's medium (DMEM), alpha MEM, RPMI1640 medium, 199 medium or F12 medium) such that the inhibitor concentration becomes within the range where p38 is sufficiently inhibited and cytotoxicity is not observed, followed by culturing the cells in the culture medium for a certain period. The inhibitor concentration varies depending on the type of the inhibitor employed, and is appropriately selected within the range of, for example, about 10 nM to about 10 µM. The contacting period is not restricted as long as it is sufficient for proliferation of the subject cells, and appropriately selected within the range of, for example, 2 days to 5 days.

The subject cells can be brought into contact with the dominant negative mutant of p38 using the same method as in the case of the above-mentioned dominant negative mutant of CaMK2.

In another mode of the present invention, the above-mentioned GSK3β inhibitor, ERK dephosphorylation inhibitor, Raf activator, CaMK2 inhibitor and p38 inhibitor may enhance expression of CyclinA2, CyclinD2, CyclinD3, Cdk2 and cdk4 and decrease expression of Ink4b.

The subject cells of the present invention are cardiomyocytes and/or cardiac progenitor cells, and preferred examples thereof include cardiomyocytes and/or cardiac progenitor cells obtained by differentiation induction of pluripotent stem cell.

<Pluripotent Stem Cells>

The pluripotent stem cells which may be used in the present invention have pluripotency which enables the cells to differentiate into any cells existing in the living body, and also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells") and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, and have pluripotency and growth ability by self-renewal.

ES cells are embryo-derived stem cells originated from the inner cell mass of a blastocyst which is an embryo formed following the 8-cell stage and the morula stage of a fertilized egg, and have ability to differentiate into any cells constituting an adult, that is, so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A.

Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; and J. A. Thomson and V. S. Marshall (1998), Curr. Top. Dev. Biol., 38:133-165).

ES cells can be established by removing the inner cell mass from the blastocyst of a fertilized egg of a subject animal, followed by culturing the inner cell mass on fibroblasts as feeders. The cells can be maintained by subculturing using a culture medium supplemented with substances such as leukemia inhibitory factor (LIF) and basic fibroblast growth factor (bFGF). Methods of establishment and maintenance of human and monkey ES cells are described in, for example, H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; and H. Kawasaki et al. (2002), Proc. Natl. Acad. Sci. USA, 99:1580-1585.

Human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF, at 37° C. under a moist atmosphere with 5% $CO_2$. Further, it is necessary to subculture ES cells every 3 to 4 days, and the subculture can be carried out using, for example, 0.25% trypsin and 0.1 mg/ml collagenase IV in PBS supplemented with 1 mM $CaCl_2$ and 20% KSR.

Selection of ES cells can be generally carried out using expression of a gene marker(s) such as alkaline phosphatase, Oct-3/4 and/or Nanog as an index/indices. In particular, selection of human ES cells can be carried out by detecting expression of a gene marker(s) such as OCT-3/4 and/or NANOG by Real-Time PCR, or by detecting a cell surface antigen(s) SSEA-3, SSEA-4, TRA-1-60 and/or TRA-1-81 by immunostaining (Klimanskaya I, et al. (2006), Nature. 444: 481-485).

Human ES cell lines such as KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and have a property to enable preparation of a chimeric mouse by transplanting the cells to a mouse blastocyst (M. Kanatsu-Shinohara et al. (2003) Biol. Reprod., 69:612-616; K. Shinohara et al. (2004), Cell, 119: 1001-1012). Germline stem cells are capable of self-renewal in a culture medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition), 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing certain specific nuclear reprogramming substances in the forms of DNAs or proteins to somatic cells, or by increasing expression of the endogenous mRNAs and proteins of the nuclear reprogramming substances by using an agent(s). iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007) Cell, 131:861-872; J. Yu et al. (2007) Science, 318:1917-1920; M. Nakagawa et al. (2008) Nat. Biotechnol., 26:101-106; WO 2007/069666; and WO 2010/068955). The nuclear reprogramming substances are not restricted as long as these are genes specifically expressed in ES cells, or genes playing important roles in maintenance of the undifferentiated state of ES cells, or gene products thereof, and examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb and Esrrg. These reprogramming substances may be used in combination when iPS cells are to be established. For example, the combination may contain at least one, two or three of the above reprogramming substances, and the combination preferably contains four of the above reprogramming substances.

The information on the nucleotide sequences of mouse and human cDNAs of the above-described respective nuclear reprogramming substances, and the amino acid sequences of the proteins encoded by the cDNAs can be obtained by referring to the NCBI accession numbers described in WO 2007/069666. Further, the information on the mouse and human cDNA sequences and amino acid sequences of each of L-Myc, Lin28, Lin28b, Esrrb and Esrrg can be obtained by referring to the NCBI accession numbers described below. Those skilled in the art can prepare desired nuclear reprogramming substances by a conventional method based on the information on the cDNA sequences or amino acid sequences.

| Gene name | Mouse | Human |
|---|---|---|
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

These nuclear reprogramming substances may be introduced into somatic cells in the form of protein by a method such as lipofection, binding to a cell membrane-permeable peptide, or microinjection, or in the form of DNA by a method such as use of a vector including a virus, plasmid and artificial chromosome; lipofection; use of liposomes; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (Proc Jpn Acad Ser B Phys Biol Sci. 85, 348-62, 2009). Examples of the artificial chromosome vector include human artificial chromosomes (HACs), yeast artificial chromosomes (YACs) and bacterial artificial chromosomes (BACs, PACs). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site. Examples of the promoter to be used include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred. The vectors may further contain, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; or the like. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect (Kaji, K. et al., (2009), Nature, 458: 771-775; Woltjen et al., (2009), Nature, 458: 766-770; and WO 2010/012077). Further, the vector may contain the origin of lymphotrophic herpes virus, BK virus or Bovine papillomavirus and sequences involved in their replication, such that the vector can replicate without incorporation into the chromosome and exist episomally. Examples of such a vector include vectors containing EBNA-1 and oriP sequences and vectors containing Large T and SV40ori sequences (WO 2009/115295; WO 2009/157201; WO 2009/149233). Further, in order to introduce plural nuclear reprogramming substances at the same time, an expression vector which allows polycistronic expression may be used. In order to allow polycistronic expression, the sequences encoding the genes may be linked to each other via IRES or the foot-and-mouth disease virus (FMDV) 2A coding region (Science, 322:949-953, 2008; and WO 2009/092042 and WO 2009/152529).

For enhancing the induction efficiency of iPS cells upon the nuclear reprogramming, histone deacetylase (HDAC) inhibitors [for example, low molecular inhibitors such as valproic acid (VPA) (Nat. Biotechnol., 26(7): 795-797 (2008)), trichostatin A, sodium butyrate, MC 1293 and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], Wnt Signaling activators (e.g., soluble Wnt3a) (Cell Stem Cell, 3, 132-135 (2008)), growth factors such as LIF and bFGF, ALK5 inhibitors (e.g., SB431542) (Nat. Methods, 6: 805-8 (2009)), mitogen-activated protein kinase signaling inhibitors, glycogen synthase kinase-3 inhibitors (PLoS Biology, 6(10), 2237-2247 (2008)), miRNAs such as miR-291-3p, miR-294 and miR-295 (R. L. Judson et al., Nat. Biotech., 27: 459-461 (2009)), and the like may be used in addition to the above-described factors.

Examples of the agent used for increasing expression of the endogenous proteins of nuclear reprogramming substances include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2 and prostaglandin E2 (WO 2010/068955).

Examples of the culture medium for induction of the iPS cells include (1) DMEM, DMEM/F12 and DME supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells (ReproCELL Inc., Kyoto, Japan), mTeSR-1).

Examples of the culture method include a method wherein somatic cells and nuclear reprogramming substances (DNAs or proteins) are brought into contact with each other at 37° C. in the presence of 5% $CO_2$ in DMEM or DMEM/F12 medium supplemented with 10% FBS, and the cells are cultured for about 4 to 7 days, followed by replating the cells on feeder cells (e.g., mitomycin C-treated STO cells or SNL cells) and starting culture in a bFGF-containing culture medium for primate ES cells about 10 days after the contact between the somatic cells and the reprogramming substances, thereby allowing ES cell-like colonies to appear about 30 to about 45 days after the contact, or later. To enhance the induction efficiency of iPS cells, the culture may be carried out under a condition wherein the concentration of oxygen is as low as 5 to 10%.

As an alternative culture method, the somatic cells may be cultured on feeder cells (e.g., mitomycin C-treated STO cells or SNL cells) in DMEM medium supplemented with 10% FBS (which may further contain LIF, penicillin/streptomycin, puromycin, L-glutamine, non-essential amino acids, β-mercaptoethanol and/or the like, as appropriate), thereby allowing ES-like colonies to appear after about 25 to about 30 days of the culture, or later.

During the above culture, the culture medium is replaced with a fresh culture medium once every day from Day 2 of the culture. The number of the somatic cells used for nuclear reprogramming is not restricted, and usually within the range of about $5 \times 10^3$ to about $5 \times 10^6$ cells per 100-cm$^2$ area on the culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present specification means any cells, excluding germ cells, derived from a mammal (e.g., human, mouse, monkey, pig or rat). Examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cells) or terminally-differentiated mature cells may be used as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

In the present invention, the mammalian individual from which somatic cells are derived is not restricted, and preferably human.

(E) ES Cells Derived from Cloned Embryo Obtained by Nuclear Transfer ntES cells are ES cells derived from a cloned embryo prepared by the nuclear transfer technique, and have almost the same properties as those in ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition), 47-52). In nuclear transfer, reprogramming can be achieved by injecting the nucleus of a somatic cell into a mammalian enucleated unfertilized egg and culturing the resultant for a several hours.

(F) Fused Stem Cells

These are stem cells prepared by fusing a somatic cell with an egg or an ES cell, and have the same pluripotency as that of the ES cell used for the fusion and also have genes specific to somatic cells (Tada M et al. Curr Biol. 11:1553-8, 2001; Cowan C A et al. Science. 2005 Aug. 26; 309(5739):1369-73).

<Method of Differentiation Induction into Cardiomyocytes and Cardiac Progenitor Cells>

In the present invention, "cardiomyocytes" means cells of cardiac muscle having the property of self-beating. "Cardiac progenitor cells" means progenitor cells of such cardiomyocytes, and have an ability to produce cardiomyocytes and vascular smooth muscle that form beating muscle and electrically conductive tissues. Here, the cardiomyocytes and the cardiac progenitor cells may be either coexisting with or separated from each other.

The cardiomyocytes and the cardiac progenitor cells are characterized in that these are positive for cardiac troponin (cTNT or troponin T type 2), which is a myocardial marker, and/or for αMHC (a myosin heavy chain). When proliferation of cardiomyocytes or cardiac progenitor cells is to be measured, the expression level(s) of one or more of these markers, or the expression level(s) of a reporter gene(s) linked to the promoter(s) of these marker(s) can be used as an index/indices.

In order to induce differentiation of pluripotent stem cells such as ES cells or iPS cells into cardiomyocytes or cardiac progenitor cells, the following method can be used.

The pluripotent stem cells obtained as mentioned above may be separated by an arbitrary method and subjected to adherent culture and/or co-culture with feeder cells, using a coated culture dish, and/or suspension culture. The separation may be carried out either mechanically or by using a separation liquid having a protease activity and a collagenase activity (e.g., Accutase™ or Accumax™) or a separation liquid having only a collagenase activity or EDTA solution (for example 0.5 mM EDTA solution). The adherent culture is carried out in an arbitrary culture medium in the coated culture dish. Examples of the coating agent include Matrigel (BD), type I collagen, type IV collagen, gelatin, laminin, heparin sulfate proteoglycan and entactin, and combinations thereof. The coating agent is preferably gelatin or type IV collagen. Examples of the cells used in the co-culture include OP9 cells (Nishikawa, S. I. et al, Development 125, 1747-1757 (1998)) and END-2 cells (Mummery C, et al, Circulation. 107:2733-40 (2003)). The suspension culture can be carried out using a culture dish that has not been artificially treated (e.g., by a coating-treatment with extracellular matrix or the like) in order to improve its property of adhering to cells, or that has been treated (e.g., by a coating-treatment using polyhydroxyethyl methacrylate (poly-HEMA)) to artificially suppress adhesion. However, the examples are not particularly limited thereto. In other embodiment, combination method with the suspension culture and the adherent culture is performed. Preferably, the adherent culture is performed after the suspension culture.

The culture medium in this process can be prepared by using, as a basal medium, a culture medium used for culturing animal cells. Examples of the basal medium include IMDM medium, Medium 199 medium, Eagle's Minimum Essential Medium (EMEM), αMEM medium, Dulbecco's modified Eagle's Medium (DMEM), Ham's F12 medium, RPMI 1640 medium and Fischer's medium, and mixed media thereof. The culture medium is preferably αMEM or DMEM. The culture medium may be either a serum-containing medium or a serum-free medium. As required, the culture medium may contain one or more of serum replacements such as albumin, transferrin, Knockout Serum Replacement (KSR) (a serum replacement of FBS for culturing ES cells), B-27 Supplement (Invitrogen), fatty acid, insulin, collagen precursor, minor element, 2-mercaptoethanol and 3'-thiolglycerol; and may contain one of more of substances such as a lipid, amino acid, L-glutamine, Glutamax (Invitrogen), non-essential amino acid, vitamin, growth factor, antibiotic, antioxidant, pyruvic acid, buffer, inorganic salt, Dkk1 and cyclosporin A. Examples of preferred growth factors in the present invention include bFGF, activin A and BMP4.

Preferred examples of the culture medium include αMEM medium supplemented with 10% FBS, αMEM medium supplemented with 1 to 3 μg/mL cyclosporin A and 10% FBS, and DMEM medium supplemented with 10% FBS.

The culture temperature is not restricted and may be about 30 to 40° C., preferably about 37° C., and the culture is carried out under atmosphere of $CO_2$-containing air, wherein the $CO_2$ concentration is preferably about 2 to 5%. The culture is carried out for a number of days required for cardiac troponin and/or αMHC to be expressed, and the culturing period is 10 days to 20 days, for example.

Examples of preferred conditions of the culture include culturing the cells in αMEM medium supplemented with 10% FBS for 4 days and then isolating Flk1-positive cells, followed by co-culturing the isolated cells with OP9 cells in αMEM medium supplemented with 3 μg/mL cyclosporin A and 10% FBS for 6 days or co-culturing the isolated cells with END-2 cells in DMEM medium supplemented with 10% FBS for 16 days.

<Screening Method for Cardiomyocyte- and/or Cardiac Progenitor Cell-Proliferating Agent>

The present invention provides a method for screening a cardiomyocyte- and/or cardiac progenitor cell-proliferating agent.

The cardiomyocyte- and/or cardiac progenitor cell-proliferating agent can be used for proliferating cardiomyocytes and cardiac progenitor cells obtained by differentiation induction of pluripotent stem cells and also can be used as a therapeutic agent for diseases caused by defect of cardiomyocytes, and examples of the diseases caused by defect of cardiomyocytes include, but are not limited to, myocarditis and cardiac infarction.

An example of the method for screening cardiomyocyte- and/or cardiac progenitor cell-proliferating agent includes a method comprising the steps of:

(1-1) contacting a test substance with cardiomyocytes and/or cardiac progenitor cells obtained by differentiation induction of pluripotent stem cells;

(1-2) counting the number of cardiomyocytes and/or cardiac progenitor cells after step (1-1); and (1-3) selecting the test substance as a cardiomyocyte- and/or cardiac progenitor cell-proliferating agent when the number of cardiomyocytes and/or cardiac progenitor cells is larger than the number (reference number) of cardiomyocytes and/or cardiac progenitor cells which are not contacted with the test substance.

A preferable example of cardiomyocytes and/or cardiac progenitor cells obtained by differentiation induction of pluripotent stem cells is cardiomyocytes and/or cardiac progenitor cells obtained by culturing pluripotent stem cells in αMEM containing 10% FBS for about four days, then, isolating Flk1-positive cells and culturing the Flk1-positive cells in αMEM containing 3 μg/mL cyclosporine A and 10% FBS for about six days in the presence of OP9 cells.

Another example of the method for screening cardiomyocyte- and/or cardiac progenitor cell-proliferating agent includes a method comprising the steps of:

(2-1) contacting a test substance with cardiomyocytes and/or cardiac progenitor cells obtained by differentiation induction of pluripotent stem cells;

(2-2) counting the number of cardiomyocytes and/or cardiac progenitor cells after step (2-1); and (2-3) selecting the test substance as a cardiomyocyte- and/or cardiac progenitor cell-proliferating agent when the number of cardiomyocytes and/or cardiac progenitor cells is equivalent to or larger than the number (reference number) of cardiomyocytes and/or cardiac progenitor cells which are contacted with a positive control agent having cardiomyocyte- and/or cardiac progenitor cell-proliferating ability.

The number can be said to be equivalent to the reference number as long as the number is substantially equivalent to the reference number, and the difference between the counted number and the reference number is, for example, within about ±5%, more preferably within about ±1% of the reference number.

Examples of positive control agent include GSK3β inhibitor, ERK dephosphorylation inhibitor, Raf activator, CaMK2 inhibitor and p38 inhibitor.

The number of cardiomyocytes and/or cardiac progenitor cells can be counted, for example, by counting the number of cardiomyocytes and/or cardiac progenitor cells per a certain area under a microscope or by counting myocardial marker-positive cells per certain number of cells using flow cytometer. Examples of myocardial markers include cardiac troponin, αMHC, CD166(ALCM) (Rust W, et al, Regen Med. 4, 225-37 (2009)), N-cadherin (JP2010-158206A and Honda M, et al, Biochem Biophys Res Commun. 29, 351, 877-82 (2006)) and VCAM1 (CD106) (U.S. 61/470,101).

In the screening method of the present invention, an arbitrary test substance can be used, and examples of the test substance include cell extracts, cell culture supernatants, microbial fermentation products, extracts derived from marine organisms, plant extracts, purified proteins and crude proteins, peptides, nonpeptide compounds, synthetic low molecular compounds and naturally occurring compounds. The test compounds can be obtained by using any of a number of approaches in combinatorial library methods known in the art, such as (1) the biological library method, (2) the synthetic library method using deconvolution, (3) the "one-bead one-compound" library method and (4) the synthetic library method using affinity chromatography selection. Application of the biological library method using affinity chromatography selection is limited to peptide libraries, but the other types of approaches can be applied to low-molecular compound libraries of peptides, nonpeptide oligomers or compounds (Lam (1997) Anticancer Drug Des. 12: 145-67). Examples of synthetic methods of molecular libraries are shown in the art (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). The compound libraries may be prepared as solutions (see Houghten (1992) Bio/Techniques 13: 412-21) or beads (Lam (1991) Nature 354: 82-4), chips (Fodor (1993) Nature 364: 555-6), bacteria (U.S. Pat. No. 5,223,409 B), spores (U.S. Pat. No. 5,571,698 B, U.S. Pat. No. 5,403,484 B and U.S. Pat. No. 5,223,409 B), plasmids (Cull et al. (1992) Proc. Natl. Acad. Sci. USA 89: 1865-9) or phages (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US 2002-103360).

Kit for Screening Drugs

The present invention provides a kit for screening cardiomyocyte- and/or cardiac progenitor cell-proliferating agent. This kit may comprise the above-mentioned cells, reagents and culture medium. The kit may further comprise a document or an instruction that describes a protocol for differentiation induction.

The following Examples are described for the purpose of explaining the present invention, and do not restrict the scope of the present invention.

EXAMPLES

Cells and Culture

As the mouse ES cells, EMG-7 (Yamashita J, FASEB J, 2005) was used, which was prepared by knocking IRESBS-DpA into the Oct3/4 gene region in one of the alleles of E14Tg2a to prepare the ES cell line EB3 (Niwa H, et al, Nat Genet. 24:372-6 (2000)) followed by introducing thereto a vector in which expression of GFP is controlled by the promoter of alpha-MHC. The human iPS cells (253G1) were provided by Prof. Yamanaka in Kyoto University and cultured by a conventional method (Nakagawa M, et al. Nat Biotechnol. 26:101-6 (2008)). 253G1 cells are available from RIKEN BRC.

Method of Differentiation Induction into Cardiomyocytes

The mouse ES cell line EMG-7 was cultured on a 0.1% gelatin-coated dish using alpha MEM medium supplemented with 10% FBS for 108 to 110 hours. Thereafter, Flk1-positive cells were separated using FACS, and the separated cells were cultured on OP9 cells using a 3 μg/ml Cyclosporine A-containing medium (alpha MEM supplemented with 10% FBS) for 6 days, to induce differentiation into cardiomyocytes. These cells are hereinafter referred to as Flkd6.

Using the human iPS cell line 253G1, differentiation induction into cardiomyocytes was carried out according to the method described in Mummery C, et al, Circulation. 107:2733-40 (2003). Briefly, the 253G1 cells were co-cultured with END-2 cells for 16 days using DMEM medium supplemented with 10% FCS.

Example 1

Screening of Agents which Promote Proliferation of Cardiomyocytes

The above-mentioned Flkd6, obtained by differentiation of EMG-7, was subjected to purification by FACS using alpha-MHC-GFP as an index. To the obtained cells, 282 candidate agents were added, and the cells were cultured for 5 days, and nine types of agents which showed not less than 1.5 times larger numbers of alpha-MHC-GFP-positive cells compared to the non-addition group was selected. Among these, seven agents having different action mechanisms were selected. Further, among the seven agents, 1 μM BIO (Calbiochem), 5 μM SU1498 (Calbiochem) and 5 μM KN93 (wako), which significantly increased the number of alpha-MHC-GFP-positive cells after their addition, were selected again (FIG. 1a). These three agents were added to Flkd6, and the cells were then cultured for 2 days (Flkd6+2) or 5 days (Flkd6+5), followed by measuring the number of alpha-MHC-GFP-positive cells by FACS. As a result, significant increase in the number of the positive cells was observed especially for Flkd6+5 (FIG. 1b).

Example 2

Influence of Agents which Promote Proliferation of Cardiomyocytes on Cell Cycle

In order to examine the influence on the cell cycle, the number of cells positive for phosphorylation of histone 3 (pH3) (M phase) or ethynyl uridine (EdU) (S phase) was assayed (FIG. 2a-d). It was found that BIO promotes the S phase and the M phase from the early stage after its addition.

Example 3

Effects of Other Agents Having Same Action

Figure 3:
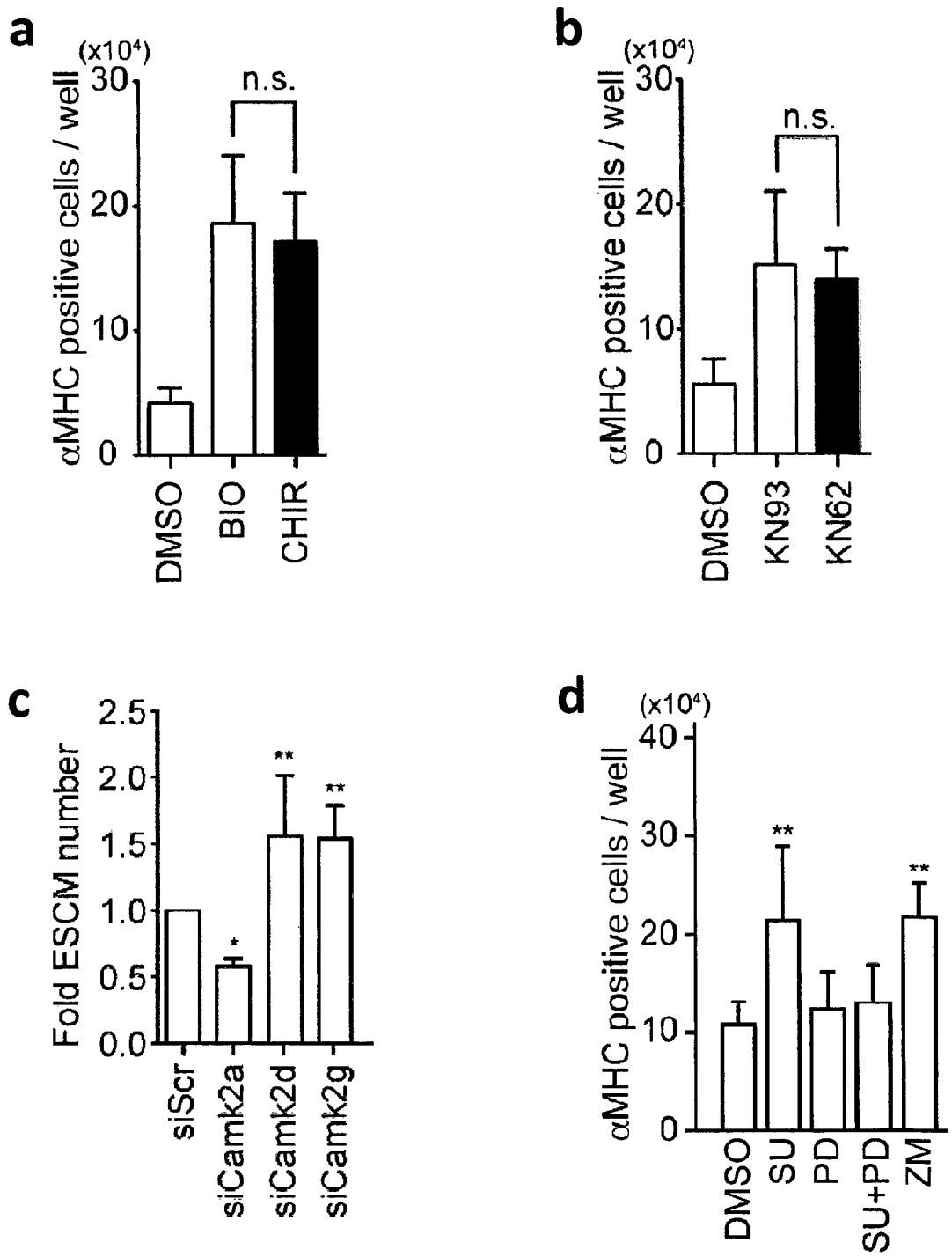
FIGS. 3a and 3b are graphs showing the number of alpha-MHC-GFP-positive cells per well obtained when Flkd6, whose differentiation was induced from EMG-7, was cultured after addition of each of CHIR (CHIR99021) and KN62. DMSO is a control wherein only a solvent was added.
FIG. 3c is a graph showing the number of cardiomyocytes whose differentiation was induced from EMG-7, where each subtype of CaMK2 was suppressed with siRNA. siScr represents the control cardiomyocyte number observed when siRNA having a random sequence (without a target gene) was used. Vertical axis shows fold increase of the number of ES cell derived cardiomyocyte (ESCM).
FIG. 3d is a graph showing the number of alpha-MHC-GFP-positive cells per well obtained when Flkd6, whose differentiation was induced from EMG-7, was cultured after addition of each of SU (SU1498), PD (PD98059), SU+PD and ZM (ZM336372). DMSO is a control wherein only a solvent was added.

The effects of a GSK3β inhibitor and a $Ca^{2+}$/calmodulin-dependent protein kinase 2 (CaMK2) inhibitor were similarly examined for Flkd6+5, and, as a result, it was found that CHIR99021 (Stemgen) and KN62 (wako) also have similar effects (FIGS. 3a and 3b). Further, in cases where siRNAs for each subtype of CaMK2 (Table 1) were used to suppress the gene, the effect of promotion of proliferation of cardiomyocytes was significantly higher in the cases where Camk2d or Camk2g was suppressed (FIG. 3c). Further, in order to examine the mechanism of SU1498, SU1498 was added together with a MEK inhibitor PD98059, and this resulted in loss of the effect (FIG. 3d). Thus, it was suggested that SU1498 promotes proliferation of cardiomyocytes by maintaining phosphorylation of ERK. Based on this result, a Raf activator ZM336372 (Calbiochem) was also studied, and it was confirmed that this also has a cardiomyocyte-proliferation-promoting effect (FIG. 3d) similarly to SU1498.

TABLE 1

| Target gene | Pooled siRNA target sequences | SEQ ID NO |
|---|---|---|
| Camk2a | GGCCUGGACUUUCAUCGAU | 1 |
|  | GCAAAUGGCAGAUCGUCCA | 2 |
|  | GUGCGACCCUGGAAUGACA | 3 |
|  | GCGGAGGAAACAAGAAGAA | 4 |
| Camk2d | GAUCAAGGCCGGAGCUUAC | 5 |
|  | GCUAGAAUCUGCCGUCUCU | 6 |
|  | CGACGAGUAUCAGCUCUUU | 7 |
|  | GAAGCGGGAUGCCAAAGAC | 8 |
| Camk2g | CGGUAGAGUGCUUACGCAA | 9 |
|  | GCAAGGGUGCUGCGGUCAA | 10 |
|  | ACUUGCUGCUGGCGAGUAA | 11 |
|  | AGUAUGAGAAAGACGCAAA | 12 |

Example 4

Combinatorial Effects and Expression of Cell Cycle-Related Genes

Since the effect of promotion of proliferation of cardiomyocytes is also reported for p38 inhibitors (Engel F B, et al, Proc Natl Acad Sci USA. 103:15546-51 (2006)), SB203580, which is a p38 inhibitor, was included in the study, and combinatorial effects by the following combinations were studied. The concentrations of the agents were the same as those described in Example 1.
(1) BIO+SU1498
(2) BIO+KN93
(3) SU1498+KN93
(4) BIO+SU1498+KN93
(5) SB203580
(6) BIO+SU1498+SB203580
(7) BIO+KN93+SB203580

Figure 4:
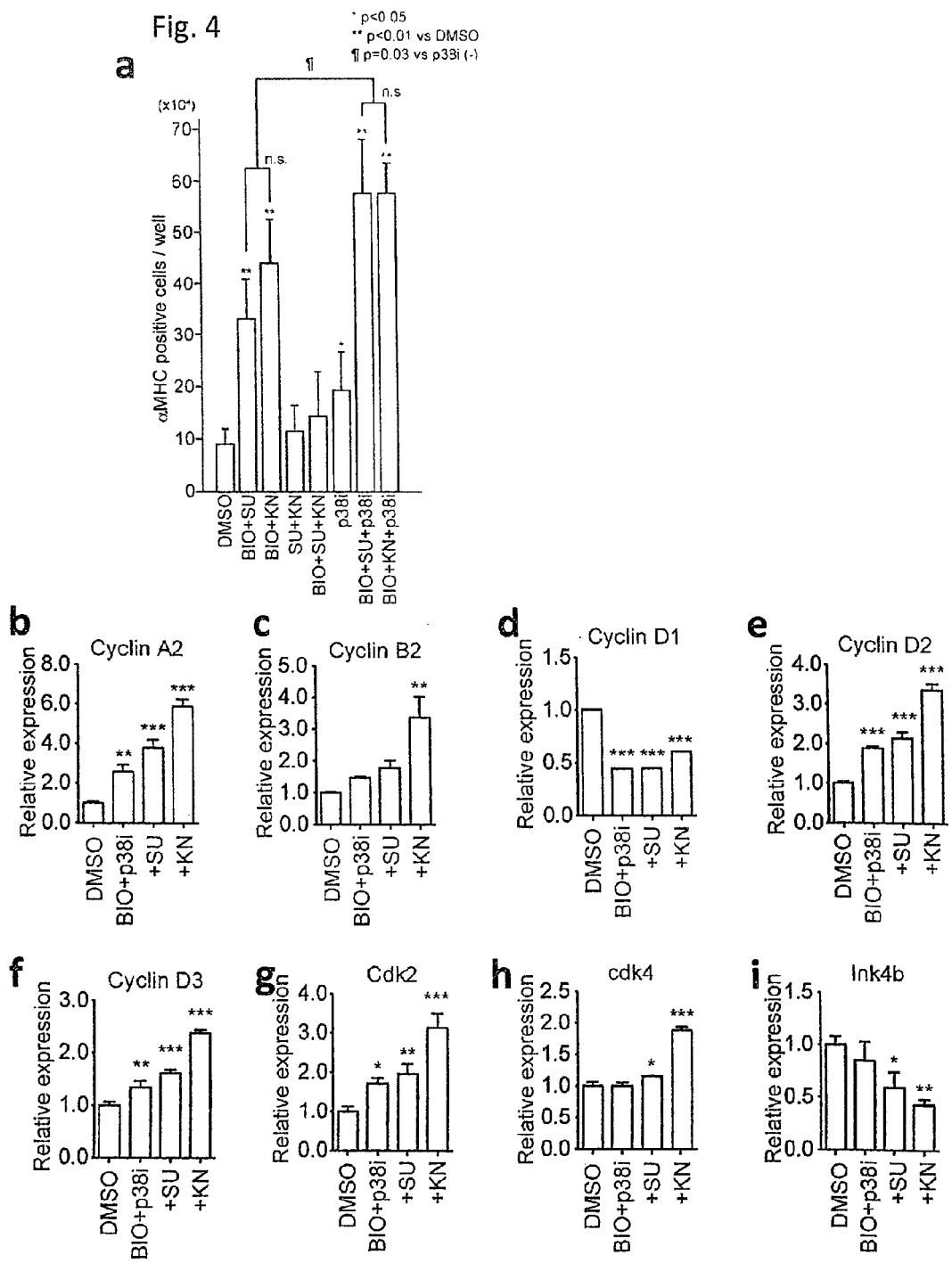
FIG. 4a is a graph showing the number of alpha-MHC-GFP-positive cells per well obtained when Flkd6, whose differentiation was induced from EMG-7, was cultured after addition of each of BIO+SU (SU1498), BIO+KN93, SU+KN93, BIO+SU+KN93, p38i (SB203580), BIO+SU+ p38i and BIO+KN93+p38i. DMSO is a control wherein only a solvent was added.
FIGS. 4b to 4i are graphs showing the expression levels of mRNAs of CyclinA2 (b), CyclinB2 (c), CyclinD1 (d), CyclinD2 (e), CyclinD3 (f), Cdk2 (g), cdk4 (h) and Ink4b (i) in the cells obtained when Flkd6, whose differentiation was induced from EMG-7, was cultured after addition of each of BIO+p38i, BIO+SU and BIO+KN93. The expression levels are shown as the relative values to those observed in the case where DMSO was added.

In any of these combinations, the number of alpha-MHC-GFP-positive cells was higher in EMG-7-derived Flkd6+5 when compared to the case of the control wherein only the solvent was added. It was found that the effect was especially high in the combinations of (1), (2), (6) and (7) (FIG. 4a).

Subsequently, influences on expression of the cell cycle-related genes CyclinA2, CyclinB2, CyclinD1, CyclinD2, CyclinD3, Cdk2, cdk4 and Ink4b were examined by PCR, and, as a result, it was found that the combinations BIO+SU and BIO+KN93 show significantly larger increase in the expression levels of CyclinA2, CyclinD2, CyclinD3, Cdk2 and cdk4, compared to the control. Conversely, it was also found that the expression level of Ink4b is decreased (FIGS. 4b to 4i).

Example 5

Effect on Cardiomyocytes Derived from Human iPS Cells

By the above-mentioned method, 253G1 was allowed to differentiate into cardiomyocytes, and each agent was added to the cells for 4 days, followed by measuring the number of troponin T type 2 (cTnT)-positive cells. As a result, the cell number was relatively larger in the cases where BIO, SU1498, BIO+SU1498+SB203580 and BIO+KN93+

SB203580 were used compared to the case of the control, and, in particular, the case where BIO+SU1498+SB203580 was used showed a significantly larger number of the cells (FIG. 5a). The positive rates of pH3 and EdU by immunostaining were studied, and it was then revealed that the positive rate of EdU was higher in BIO (16.0±0.5%), SU1498 (14.3±0.4%), SB203580 (14.6±2.1%), BIO+SU1498+SB203580 (19.9±1.4%) and BIO+KN93+SB203580 (16.3±4.3%) compared to the control (11.3±1.0%) (FIG. 5b).

INDUSTRIAL APPLICABILITY

GSK3β inhibitor, ERK dephosphorylation inhibitor, Raf activator, CaMK2 inhibitor or p38 inhibitor can be used as a proliferation-promoting agent for cardiomyocytes or cardiac progenitor cells whose differentiation was induced from pluripotent stem cells such as ES cells.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

What is claimed is:

1. A method for proliferating cardiomyocytes and/or cardiac progenitor cells, comprising contacting cultured cardiomyocytes and/or cardiac progenitor cells with GSK3β inhibitor, and p38 inhibitor, wherein the cardiomyocyte is a human cardiomyocyte and the cardiac progenitor cell is a human cardiac progenitor cell.

2. The method according to claim 1, wherein said cardiomyocytes and/or cardiac progenitor cells are cardiomyocytes and/or cardiac progenitor cells obtained by differentiation induction of pluripotent stem cells.

3. The method according to claim 1, wherein said cardiomyocytes and/or cardiac progenitor cells are further contacted with i) CaMK2 inhibitor, and/or ii) ERK activator.

4. The method according to claim 3, wherein said CaMK2 inhibitor is KN62 or KN93, and said ERK dephosphorylation inhibitor is SU1498.

5. The method according to claim 1, wherein expression of CyclinA2, CyclinD2, CyclinD3, Cdk2 and cdk4 is enhanced and expression of Ink4b is decreased in cardiomyocytes and/or cardiac progenitor cells after contacting cardiomyocytes and/or cardiac progenitor cells with GSK3 beta inhibitor, and p38 inhibitor.

6. The method according to claim 1, wherein said GSK3β inhibitor is CHIR99021 or BIO and said p38 inhibitor is SB203580.

7. A method for screening a cardiomyocyte- and/or cardiac progenitor cell-proliferating agent, comprising the steps of:
   (1) contacting a test substance with cardiomyocytes and/or cardiac progenitor cells obtained by differentiation induction of pluripotent stem cells;
   (2) counting the number of cardiomyocytes and/or cardiac progenitor cells after step (1); and
   (3) selecting the test substance as a cardiomyocyte- and/or cardiac progenitor cell-proliferating agent when the number of cardiomyocytes and/or cardiac progenitor cells is equivalent to or larger than the number of cardiomyocytes and/or cardiac progenitor cells which are contacted with a positive control agent having cardiomyocyte- and/or cardiac progenitor cell-proliferating ability, wherein the cardiomyocyte is a human cardiomyocyte and the cardiac progenitor cell is a human cardiac progenitor cell,
   and wherein said positive control agent is at least one compound selected from the group consisting of ERK dephosphorylation inhibitor, Raf activator, and CaMK2 inhibitor.

* * * * *

```
                        SEQUENCE LISTING

<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: Camk2a-1

<400> SEQUENCE: 1
ggccuggacu uucaucgau                                                  19

<210> SEQ ID NO 2
<211> LENGTH: 19
<212> TYPE: RNA
<213> ORGANISM: Artificial Sequence
<220> FEATURE:
<223> OTHER INFORMATION: Camk2a-2

<400> SEQUENCE: 2
gcaaauggca gaucgucca                                                  19

<210> SEQ ID NO 3
<211> LENGTH: 19
<212> TYPE: RNA
<213> ORGANISM: Artificial Sequence
<220> FEATURE:
<223> OTHER INFORMATION: Camk2a-3

<400> SEQUENCE: 3
gugcgacccu ggaaugaca                                                  19

<210> SEQ ID NO 4
<211> LENGTH: 19
<212> TYPE: RNA
<213> ORGANISM: Artificial Sequence
<220> FEATURE:
<223> OTHER INFORMATION: Camk2a-4

<400> SEQUENCE: 4
gcggaggaaa caagaagaa                                                  19

<210> SEQ ID NO 5
<211> LENGTH: 19
<212> TYPE: RNA
<213> ORGANISM: Artificial Sequence
<220> FEATURE:
<223> OTHER INFORMATION: Camk2d-1

<400> SEQUENCE: 5
```
gaucaaggcc ggagcuuac                                              19

<210> SEQ ID NO 6
<211> LENGTH: 19
<212> TYPE: RNA
<213> ORGANISM: Artificial Sequence
<220> FEATURE:
<223> OTHER INFORMATION: Camk2d-2

<400> SEQUENCE: 6
gcuagaaucu gccgucucu                                              19

<210> SEQ ID NO 7
<211> LENGTH: 19
<212> TYPE: RNA
<213> ORGANISM: Artificial Sequence
<220> FEATURE:
<223> OTHER INFORMATION: Camk2d-3

<400> SEQUENCE: 7
cgacgaguau cagcucuuu                                              19

<210> SEQ ID NO 8
<211> LENGTH: 19
<212> TYPE: RNA
<213> ORGANISM: Artificial Sequence
<220> FEATURE:
<223> OTHER INFORMATION: Camk2d-4

<400> SEQUENCE: 8
gaagcgggau gccaaagac                                              19

<210> SEQ ID NO 9
<211> LENGTH: 19
<212> TYPE: RNA
<213> ORGANISM: Artificial Sequence
<220> FEATURE:
<223> OTHER INFORMATION: Camk2g-1

<400> SEQUENCE: 9
cgguagagug cuuacgcaa                                              19

<210> SEQ ID NO 10
<211> LENGTH: 19
<212> TYPE: RNA
<213> ORGANISM: Artificial Sequence
<220> FEATURE:
<223> OTHER INFORMATION: Camk2g-2

<400> SEQUENCE: 10 gcaaggugc ugcggucaa                                               19

<210> SEQ ID NO 11
<211> LENGTH: 19
<212> TYPE: RNA
<213> ORGANISM: Artificial Sequence
<220> FEATURE:
<223> OTHER INFORMATION: Camk2g-3

<400> SEQUENCE: 11
acuugcugcu ggcgaguaa                                              19

<210> SEQ ID NO 12
<211> LENGTH: 19
<212> TYPE: RNA
<213> ORGANISM: Artificial Sequence

```
<220> FEATURE:
<223> OTHER INFORMATION: Camk2g-4

<400> SEQUENCE: 12
aguaugagaa agacgcaaa                                                        19

<210> SEQ ID NO 13
<211> LENGTH: 22
<212> TYPE: PRT
<213> ORGANISM: Artificial Sequence
<220> FEATURE:
<223> OTHER INFORMATION: Camk 281-302Ala286

<400> SEQUENCE: 13

Met His Arg Gln Glu Ala Val Asp Cys Leu Lys Lys Phe Asn Ala Arg
1               5                   10                  15

Arg Lys Leu Lys Gly Ala

<210> SEQ ID NO 14
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MYRISTATE
<222> LOCATION: (1)...(1)
<223> OTHER INFORMATION: N-Myristoylated
<220> FEATURE:
<221> NAME/KEY: PHOSPHORYLATION
<222> LOCATION: (10)...(10)
<220> FEATURE:
<221> NAME/KEY: AMIDATION
<222> LOCATION: (11)...(11)

<400> SEQUENCE: 14

Gly Lys Glu Ala Pro Pro Gln Ser Pro
1               5
```